(12) United States Patent
Meredith

(10) Patent No.: US 8,512,342 B2
(45) Date of Patent: Aug. 20, 2013

(54) PORTABLE BONE GRINDER

(76) Inventor: Thomas L. Meredith, Brentwood, TN (US)

( * ) Notice: Subject to any disclaimer, the term of this patent is extended or adjusted under 35 U.S.C. 154(b) by 1162 days.

(21) Appl. No.: 12/189,772

(22) Filed: Aug. 11, 2008

(65) Prior Publication Data

US 2009/0157082 A1 Jun. 18, 2009

Related U.S. Application Data

(60) Provisional application No. 60/955,360, filed on Aug. 11, 2007.

(51) Int. Cl.
*A61B 17/00* (2006.01)

(52) U.S. Cl.
USPC .............................................. 606/84

(58) Field of Classification Search
USPC ......................................... 606/79–85; 241/27
See application file for complete search history.

(56) References Cited

U.S. PATENT DOCUMENTS

| | | | |
|---|---|---|---|
| 2,044,563 A * | 6/1936 | Carter .............................. 241/38 |
| 3,825,640 A | 7/1974 | Maierson | |
| 3,852,045 A | 12/1974 | Wheeler et al. | |
| 3,975,479 A | 8/1976 | McClean | |
| 4,522,753 A | 6/1985 | Yannas et al. | |
| 4,645,503 A | 2/1987 | Lin et al. | |
| 4,678,470 A | 7/1987 | Nashef et al. | |
| 4,843,112 A | 6/1989 | Gerhart et al. | |
| 4,947,840 A | 8/1990 | Yannas et al. | |
| 5,061,286 A | 10/1991 | Lyle | |
| 5,439,684 A | 8/1995 | Prewett et al. | |
| 5,501,706 A | 3/1996 | Arenberg | |
| 5,507,813 A | 4/1996 | Dowd et al. | |
| 5,516,532 A | 5/1996 | Atala et al. | |
| 5,545,222 A | 8/1996 | Bonutti | |
| 5,565,502 A | 10/1996 | Glimcher et al. | |
| 5,607,269 A | 3/1997 | Dowd et al. | |
| 5,658,334 A | 8/1997 | Caldarise et al. | |
| 5,662,710 A | 9/1997 | Bonutti | |
| 5,824,078 A | 10/1998 | Nelson et al. | |
| 5,899,939 A | 5/1999 | Boyce et al. | |
| 5,906,322 A | 5/1999 | Hama | |
| 5,918,821 A | 7/1999 | Grooms et al. | |
| 6,025,538 A | 2/2000 | Yaccarino, III | |
| 6,045,554 A | 4/2000 | Grooms et al. | |
| 6,090,998 A | 7/2000 | Grooms et al. | |
| 6,123,731 A | 9/2000 | Boyce et al. | |
| 6,132,472 A | 10/2000 | Bonutti | |
| 6,136,029 A | 10/2000 | Johnson et al. | |
| 6,162,227 A | 12/2000 | Eckhardt et al. | |

(Continued)

OTHER PUBLICATIONS

Thomas Matthew Industries, Inc. Model ABG04, two photos including a picture of the single internal cutting element. This model was sold as early as 1992.

*Primary Examiner* — Nicholas Woodall
(74) *Attorney, Agent, or Firm* — Waddey & Patterson, P.C.; Ryan D. Levy

(57) ABSTRACT

A bone grinder utilizing a removable cutter head unit for maintaining the processing of bone and for substantially precluding the main body of the bone grinder from being exposed to bone tissue.

14 Claims, 9 Drawing Sheets

(56) References Cited

U.S. PATENT DOCUMENTS

| | | |
|---|---|---|
| 6,187,329 B1 | 2/2001 | Agrawal et al. |
| 6,210,031 B1 | 4/2001 | Murray |
| 6,287,312 B1 | 9/2001 | Clokie et al. |
| 6,294,187 B1 | 9/2001 | Boyce et al. |
| 6,402,070 B1 | 6/2002 | Ishida et al. |
| 6,521,284 B1 | 2/2003 | Parsons et al. |
| 6,755,365 B1 | 6/2004 | Meredith |
| 7,001,551 B2 | 2/2006 | Meredith |
| 2003/0083752 A1 | 5/2003 | Wolfinbarger, Jr. et al. |
| 2003/0217415 A1 | 11/2003 | Crouch et al. |

* cited by examiner

PORTABLE BONE GRINDER

CROSS REFERENCED TO RELATED APPLICATIONS

This application is a non-provisional application which claims benefit of U.S. Patent Application Ser. No. 60/955,360 filed Aug. 11, 2007 entitled "Improved Bone Grinder Apparatus" which is hereby incorporated by reference.

The disclosure of all cited patents and publications referred to in this application are incorporated herein by reference.

BACKGROUND OF THE INVENTION

1. Technical Field

The present invention relates generally to a bone grinding apparatus having a portable design for cutting bone into bone tissue particles for application in medical procedures.

2. Background Art

Numerous medical procedures require the donation of human organs and tissues. Bone is one of the required human tissues needed for many of these medical procedures. Among other uses, donated bone samples are used as adhesives and grafting material in bone grafting operations, as protective layers in prosthetic implants, and as bone tissue composites in the creation of screws, disks, plates, pins, and joint sockets used in corrective surgeries. Regardless of the ultimate form in which donated bone is used, donated bone samples must first be processed by a grinding apparatus into bone tissue powder. The bone tissue powder is then demineralized and used in the previously mentioned capacities to facilitate the medical operation.

Several attempts have been made to create devices that correctly mill the bone samples into a useable powder form. Numerous issues have arisen that have complicated this process. First of all, many conventional bone grinding systems require a two stage milling operation using separate pieces of equipment. These prior art devices lack the ability to transform the donated sample directly into bone tissue powder. This requires the bone to be ground first into intermediary pieces within one grinding apparatus, and then the pieces must be physically transferred to a second apparatus that then converts the pieces into the bone tissue powder form required in medical procedures. Since these prior art devices require multiple pieces of equipment, which necessitates a transfer of the bone specimen between the pieces of equipment, these prior art devices fail to adequately and efficiently transform human bone into the needed bone tissue powder and contamination can occur.

A second drawback of conventional bone grinding systems is the likelihood of contamination of the bone sample during the grinding process. Throughout the grinding process, the bone sample must remain in a sterile environment. Conventional bone grinding devices fail to adequately protect that sterile environment due to the drive portion of these devices being physically located in the same area as the dispensing portion. For example, Grooms U.S. Pat. No. 5,918,821 has the motor portion of the grinding apparatus in close proximity to the dispensing portion. Thus, numerous samples of bone tissue run a high risk of contamination during the operation of the Grooms' apparatus. Also, any maintenance or repair work on any portion of the Grooms' grinding apparatus requires the entire apparatus be removed from the surgical environment in order to maintain a sterile medical facility. Therefore, the Groom's patent fails to adequately prevent the contamination of bone tissue, which is detrimental to the sterility requirement of bone tissue powder in medical applications.

Attempts to alleviate this contamination issue have been unsuccessful in the past. For example, Dowd U.S. Pat. No. 5,607,269 discloses a bone grinding apparatus that has its drive system enclosed in a box. This box initially separates the drive portion of the grinding apparatus from the location where the bone is processed. However, once the bone has been processed, the Dowd invention still requires the bone to be brought through the same environment that contains the drive mechanism before the ground bone is used for its medical purpose. Therefore, the Dowd patent fails to address the contamination issues associated with the processed bone and the drive mechanism for the grinding apparatus sharing the same surgical environment.

Another problem associated with grinding bone into usable bone tissue powder is the breakdown of morphogenetic proteins, which leads to a reduction in osteoinductivity. Osteoinductivity is a characteristic of bone tissue powder necessary to make the bone tissue powder useful within the human body. Morphogenetic proteins are the main element within the bone that maintains osteoinductivity. The major enemy to the morphogenetic proteins is the heat produced during the grinding process. The heat produced in most grinding devices is unchecked due to the lack of a controlled automated process that regulates the speed of the cutting elements and the pressure and rate at which the bone sample is fed to the cutting elements.

For example, the Grooms patent requires a human user to manually press on a plunger in order to supply the bone to its grinding elements. This manual process fails to maintain a consistent pressure or speed with which the bone sample is supplied to these grinding elements.

The Dowd apparatus also fails to maintain a consistent pressure or speed of the bone sample during the grinding process. The Dowd patent uses a holding vice to support the bone sample as a drill bit shaves off bone particles. The processing portion of the Dowd apparatus is not pressurized and lacks the controlled environment necessary in creating a consistent pressure and speed of the bone sample supplied to the grinding element. Thus, the Dowd device also fails to efficiently maintain the osteoinductive characteristic of the bone sample used in the grinding process.

Additionally, in U.S. Pat. No. 6,755,365 issued to the inventor of the present invention, a bone grinder is disclosed which is automated and which can sterilely process bone into bone tissue power for use in medical procedures, the disclosure of which is herein incorporated by reference in its entirety. The invention of the U.S. Pat. No. 6,755,365 essentially comprises a grinding chamber, primary and secondary cutting elements positioned within the grinding chamber to sequentially perform primary and secondary cutting operations on the bone, and a drive mechanism engaging primary and secondary cutting elements. While the invention of U.S. Pat. No. 6,755,365 is very able and efficient at grinding bone, there is also a need for a different type of bone grinder which may provide an easier and more efficient application for surgical procedures.

Unfortunately, many bone grinders of the prior art are additionally burdened with complicated cleaning procedures which may include sterilization through an autoclave system in order to preclude contamination of a patient by a previous patient and bone sample. In addition, many prior art bone grinders are cumbersome, lack an easy to clean design and furthermore do not adequately capture ground bone for use in medical procedures.

What is desired therefore is a bone grinder which is easier to clean while also being ideal for operating room type procedures. Indeed, a combination of characteristics including an efficient and user friendly design not realized in the prior art as well as an improvement over prior art bone grinders have been found to be necessary for bone grinders used in a variety of medical settings. Also desired is a bone grinder that is easy to move and further that does not require autoclave sterilization techniques between uses.

SUMMARY OF THE INVENTION

Generally, the invention of the present application comprises a bone grinder that may be either driven by compressed air or electrical power. Each unit may be small in overall size typically with the electrical unit being somewhat smaller than the bone grinder of the present invention when designed for pneumatic operation. In embodiments where the bone grinder of the present invention is operated through compressed air, the operating pressure range is from about 20 psi and higher with a preferably minimal operating pressure of about 80 psi, where as the electrical bone grinder of the present invention typically operates at 110/120V although may also be designed for additional or different electronic inputs.

In a variety of embodiments the bone grinders of the present invention may be constructed of a steel, plastic, FDA approved material, ceramic, or any other variety of alloys, metals or polymers which may provide a firm and rigid structure for the bone grinder. Preferably, the bone grinder of the present invention has dimensions of less than about 14" wide by 10.5" deep by 6.5" high with the electrical bone grinder having dimensions which are generally smaller than the pneumatic bone grinder. These ranges are considered preferable although the bone grinder of the present invention either in pneumatic or electrical configuration may be of slightly larger or smaller sizes and in no way is limited to the sizes described herein.

Advantageously, the bone grinders of the present invention may be sterilized and sealed to preclude ground bone from migrating past the cutter housing of the bone grinder. Generally, cutter housings will be of the same dimension for either electrical units or pneumatic units with a general sizes of the cutter housing being less than about 6" wide by 6" high by 3" deep although may be smaller or larger depending on the application and desired size of the bone grinder. Furthermore, the cutter housing of this improved bone grinder may be plastic and disposable, thus insuring greater sterility and ease of use. Additionally, the cutter housing may also be comprised of a material which may be sterilized so as to be used repetitively with the cutter heads additionally being of a disposable design in many embodiments.

Generally, the cutter concept is for small amounts or chunks of cancellous bone which are typically chiseled from a patient's hip though may be used with materials provided from a bone tissue repository. Additionally, prepackaged bone material from a local tissue bank supplier or even medical device manufacturer may be utilized with the grinder of the present invention.

Advantageously, the grinder power drive system or housing of the bone grinder of the present invention may be designed to be easily cleanable and can also remain in an operating room without having to be removed or shifted for cleaning. Furthermore, the grinder unit is simple to operate requiring little in the way of training so that a nurse or technician may utilize the grinder without occupying a doctor's time.

An object of the present invention therefore is a bone grinder having characteristics which enable it to be used in a sterile environment.

Another object of the present invention is a bone grinder having a compact size thus providing ease in transporting the grinder.

Still another object of the invention is a bone grinder having a disposable cutter arrangement.

Yet another object of the invention is a bone grinder including a detachable unit for collecting ground bone tissue.

Another object of the invention is a bone grinder using a disposable cutter head unit which has been previously prepackaged and sterilized.

These aspects and others that have become apparent to the artist and upon review of the following description can be accomplished by providing a bone grinder having a compact size which may include the use of a disposable cutter head arrangement for grinding bone. The bone grinder advantageously may be utilized in hospital surgical suites and maintained within a sterile environment without the time consuming need to continually undergo autoclave cycles. Additionally, the bone grinder of the present invention may include a cutter head arrangement with cutters rotating opposite directions so that bone may be pulled more easily through the cutting zone for grinding.

It is to be understood that both the foregoing generally description and the following detailed description provide embodiments of the invention and are intended to provide an overview or framework of understanding to the nature and character of the invention as it is claimed.

DETAILED DESCRIPTION OF THE PREFERRED EMBODIMENTS

Figure 1:
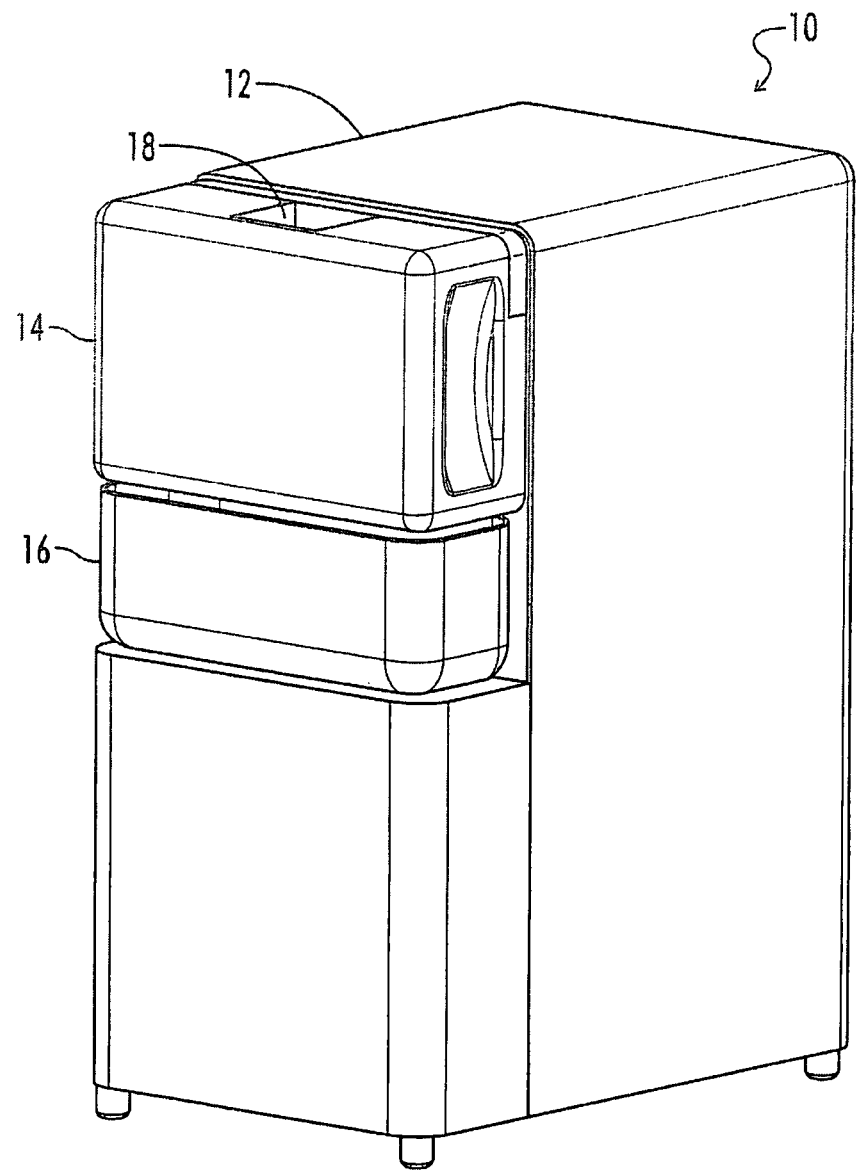
FIG. 1 is an illustration of a first embodiment of the bone grinder of the present invention.
Figure 2:
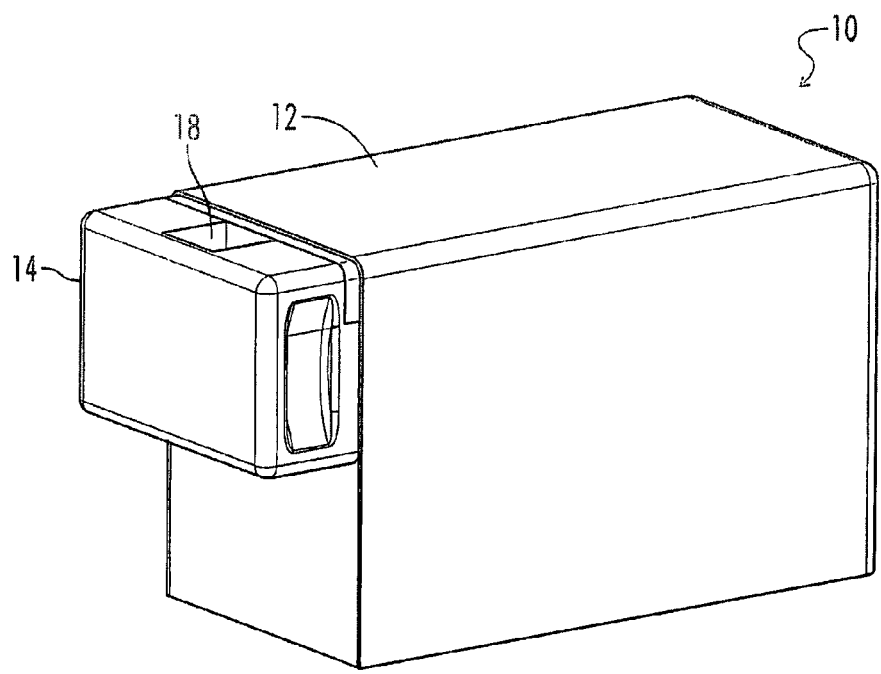
FIG. 2 is an illustration of a second embodiment of the bone grinder of the present invention.

Referring now to FIG. 1 and FIG. 2 multiple embodiments of the bone grinder of the present invention are shown and generally designated by the numeral 10. Bone grinder 10 can be described as having main body 12 and cutter unit 14 with the embodiment as illustrated in FIG. 1 also including collection receptacle 16. Generally, main body 12 includes the mechanisms for converting electrical energy or pneumatic energy into mechanical energy for grinding the bone and further typically contain the electronics and necessary equipment for controlling and activating bone grinder 10 of the present invention. Cutter head unit 14 generally includes the actual cutter heads for grinding the bone as well as housing the heads in a removable body.

Figure 3:
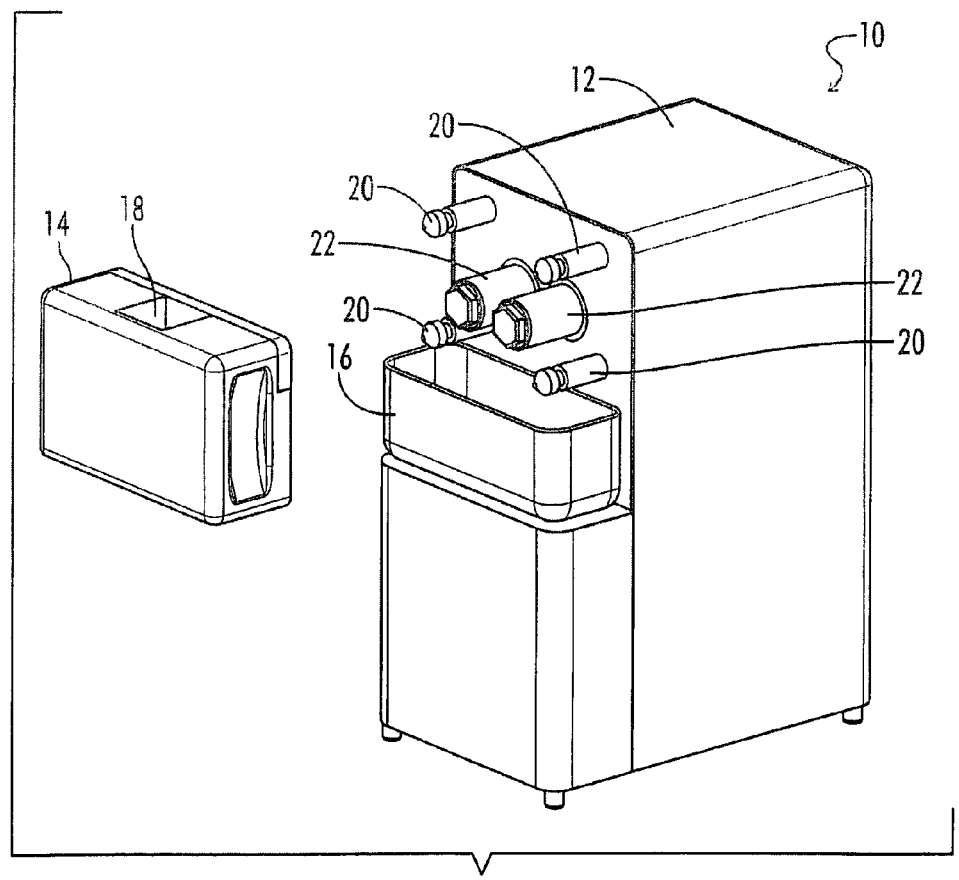
FIG. 3 is an illustration of the components of the first embodiment of the bone grinder of the present invention.
Figure 4:
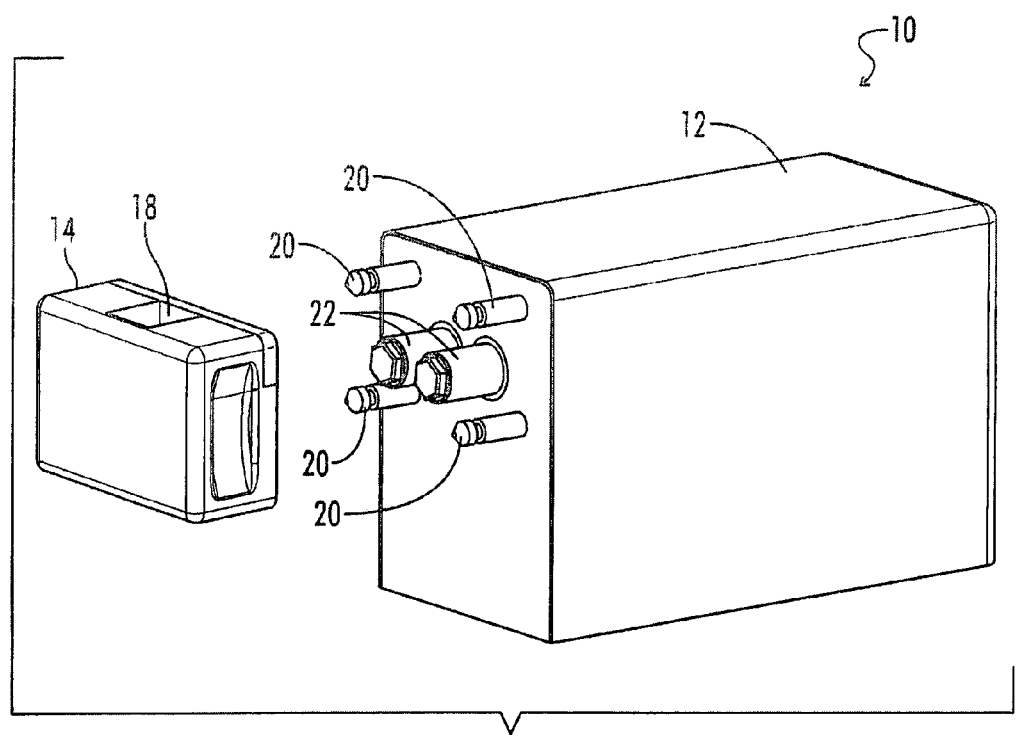
FIG. 4 is an illustration of the components of the second embodiment of the bone grinder of the present invention.
Figure 5A:
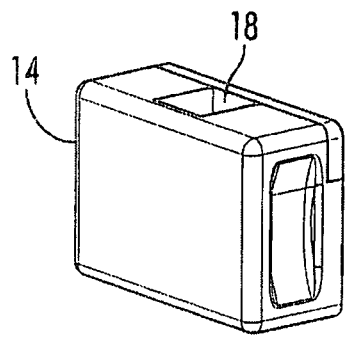
FIG. 5a is an illustration of the cutter unit of the present invention.
Figure 5B:
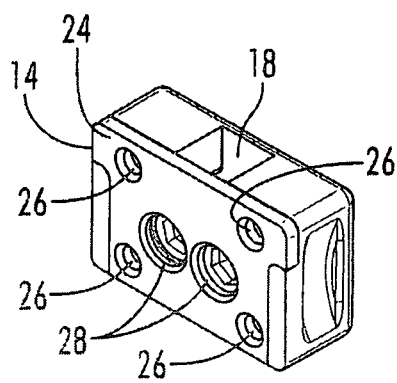
FIG. 5b is an illustration of a rear view of the cutter unit of the present invention.
Figure 5C:
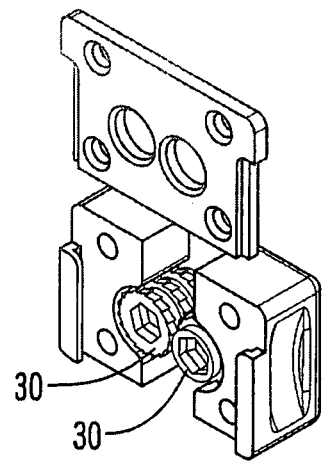
FIG. 5c is an illustration of a back view of the cutter unit of the present invention with backing plate removed.
Figure 5D:
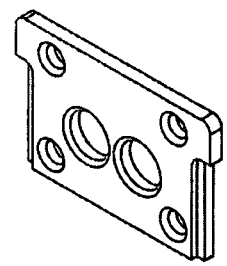
FIG. 5d is an illustration of a backing plate of the present invention.
Figure 5E:
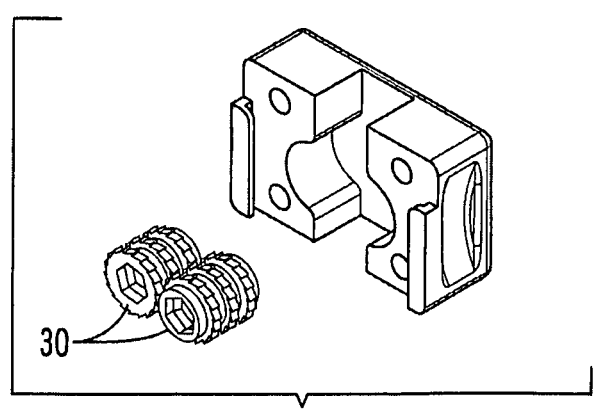
FIG. 5e is an illustration of a rear view of the cutter unit having backing plate removed and cutter heads removed of the bone grinder of the present invention.

As is seen in FIG. 3 and FIG. 4, cutter head unit 14 which preferably includes bone input 18 as well as a bone output may be removable from main body 12 of bone grinder 10. In further embodiments, bone input 18 may be located elsewhere and possibly may be included on main body 12 though it is preferable to be included on cutter unit 14 in close proximity to the cutter heads (not shown). Bone grinder 10 further includes mounting shafts 20 for attachment of cutter head unit 14 for the grinding of bone. In further embodiments not illustrated, the numbers and locations of mounting shafts 20 may vary though preferably four mounting shafts are included on main body 12 of bone grinder 10 of the present invention. Generally, mounting shafts 20 fit within complimentary openings located on the back side of cutter head unit 14 so that cutter head unit 14 fits to the main body 12 of bone grinder 10, though as discussed later preferably includes a gap. Furthermore, main body 12 of bone grinder 10 further includes drive shafts 22 for driving the cutter heads of cutter head unit 14. In further embodiments, greater or lesser numbers of cutter heads are utilized for grinding bone and a greater or lesser number of drive shafts may be present on main body 12. In yet further embodiments not illustrated drive shafts 12 may be instead located on cutter head unit 14 and insert into cavities on main body 12 rather than to be affixed to the drive mechanisms within main body 12 of bone grinder 10.

Referring now to FIGS. 5a through 5e there are multiple views of the components of cutter head unit 14 of the present invention. Generally cutter head unit 14 includes bone input 18 which generally comprises an opening so that bone may be inserted and thus contact the cutter heads for grinding with the unit also preferably including a bone output for the removal of the ground bone. As illustrated in 5b, cutter head unit 14 may also include backing plate 24 for containing the cutter heads there within cutter head unit 14. Generally, backing plate 24 includes matching apertures 26 as well as drive apertures 28 so that cutter head unit 14 may be placed on main body 12 of bone grinder 10 for the grinding of bone. In a preferable embodiment, backing plate 24 may slide to fit onto cutter head unit 14 and thus is removable where further embodiments may be permanently affixed to cutter head unit 14. Further, as illustrated best in 5c and 5e cutter heads 30 are included within a central area of cutter head unit 14 and are generally held in place by backing plate 24 to remain in about the center of cutter head unit 14.

Figure 6A:
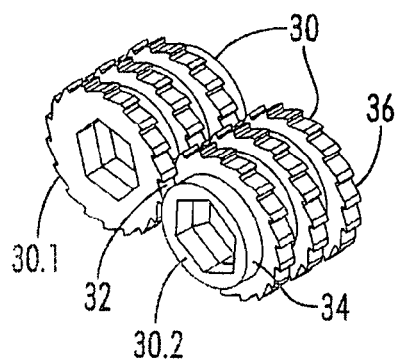
FIG. 6a is an illustration of a prospective view of a set of cutter heads of the present invention.
Figure 6B:
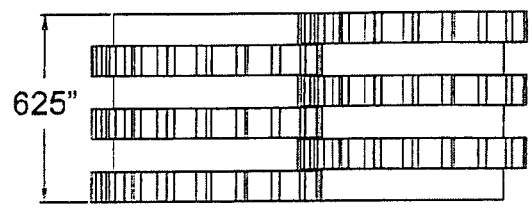
FIG. 6b is an illustration of a top view of a set of cutter heads of the present invention.
Figure 6C:
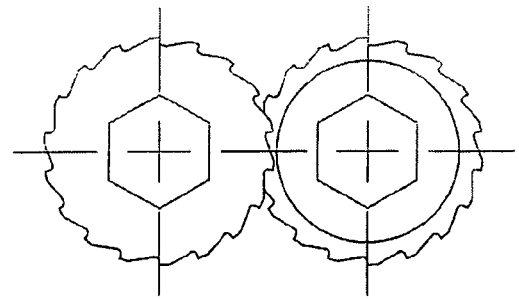
FIG. 6c is an illustration of the orientation of a set of cutter heads of the present invention.
Figure 7A:
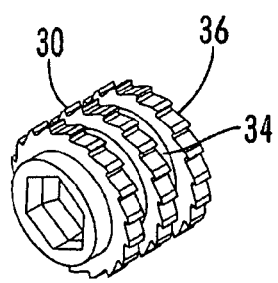
FIG. 7a is an illustration of one of the cutter heads of the present invention.
Figure 7C:
FIG. 7c is an illustration of a spacer for use with the cutter head set of the present invention.
Figure 7B:
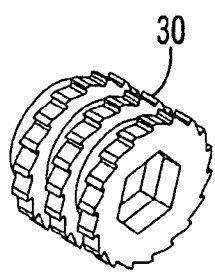
FIG. 7b is an illustration of the opposing cutter head of the present invention.

Referring now to FIGS. 6a through 6c there are multiple illustrations of a first embodiment of cutter heads 30 for the bone grinder of the present invention with FIGS. 7a and 7b illustrating each of the cutter heads of cutter head 30 in an isolated arrangement. Generally, each cutter head includes sets of teeth positioned in relationship with the complementary cutter head to define a cutting zone area between cutter heads 30 for the bone to pass. Each cutter head engages a drive shaft 22 of main body 12 of bone grinder 10 in cutter head unit 14 is placed onto main body 12. As such, the drive mechanism which may be a mechanical drive mechanism that is either electrically or pneumatically powered, turns drive shafts 22 to move the teeth of the cutter heads through the cutting zone between the cutter heads so that force is applied to bone. Preferably, each cutter head of cutter head 30 moves in an opposite direction with one cutter head moving clockwise and one cutter head moving counter clockwise. As illustrated in 6a, cutter head 30.1 would move preferably in a clockwise direction and cutter head 30.2 would preferably move in a counter clockwise direction so that both sets of teeth are moving in about the same direction through cutting zone 32. Advantageously, this would draw bone into cutting zone 32 so that significant pressure is not needed to run bone through the bone grinder of the present invention. This further aids in less bone loss and is preferable as the cutter is generally designed for hospital suite operations and as such small amounts of bone will function within cutter heads having the teeth rotate through the cutting zone in the same direction whereas in significantly larger bone grinders this would likely not be the case.

In a preferable embodiment the teeth of one cutter head engage a complementary smooth surface of the adjacent cutter head in the rotation of the cutter heads for grinding bone. However, in further arrangements the teeth may be aligned so that each tooth of one cutter head falls within the space between teeth on the second cutter head during the rotation of the cutter heads.

Cutters 30 of the present invention are instrumental in producing the bone into bone tissue powder for use in medical procedures. By design, cutter heads 30 are significantly small with each cutter head generally having a diameter of about less than 1" and more preferably less than about 0.75 inches. Additionally, each row 36 of teeth may preferably have a thickness of less than about 0.25 inches and more preferably have a thickness of less than about 0.12 inches with the total width of a cutter head being less than about 0.9 inches and more preferably less than about 0.7 inches.

In alternative embodiments of the cutter heads of the present invention the cutter heads will rotate through the cutting zone in opposite directions and furthermore be of a greater or smaller size including width of the teeth, diameter of the cutter head and length of the cutter head. Advantageously, variations in the cutter heads allow bone grinder 10 of the present invention to cut other items including but not limited to animal bone and other forms of tissue.

In particular embodiments of bone grinder 10 of the present invention cutter head spacer 36 may be utilized with the cutter head so that the cutter heads are properly oriented within cutter head unit 14. More specifically, in machine cutter head 30 for the present invention only one embodiment of cutter head 30 may be produced and thus a cutter head spacer may be utilized to put the teeth in the proper location for each cutter head. In other embodiments a cutter head spacer is generally utilized to maintain a small gap at the end of the drive shafts which insert into cutter heads 30 so that cutter heads 30 do not ride directly against cutter head unit 14 of the present invention.

Figure 8A:
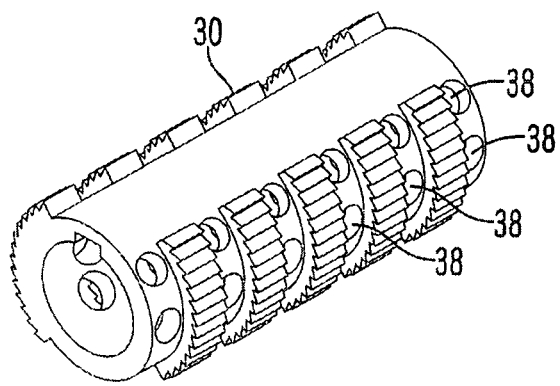
FIG. 8a is an illustration of a second embodiment of a cutter with open side cavities of the present invention.
Figure 8B:
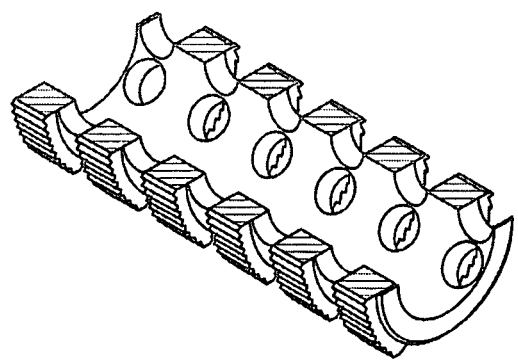
FIG. 8b is a cross sectional view of the cutter with open side cavities of the present invention.
Figure 8C:
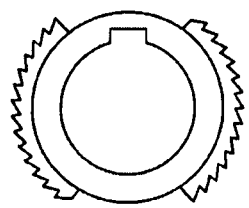
FIG. 8c is an illustration of an end view of the cutter head with side openings of the present invention.

Referring now to FIGS. 8a, 8b and 8c there is a further embodiment of cutter heads 30 which may be utilized in bone grinder 10 of the present invention. Generally, these bone grinders include an open side cavity 38 of various locations on the surface of cutter heads 30. This may allow for this embodiment of cutter head 30 to collect and maintain portions of ground bone in the cutter head body for easy collection by the user.

Figure 9A:
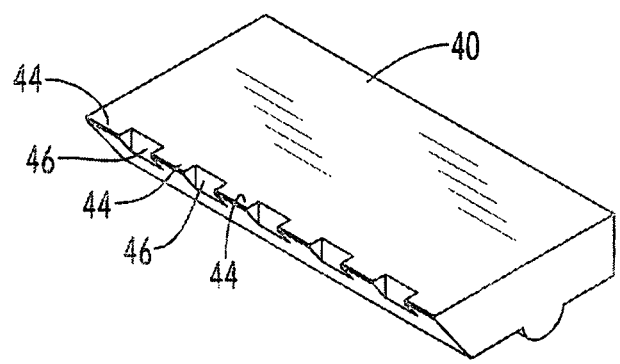
FIG. 9a is an illustration of a cutter insert of the present invention.
Figure 9B:
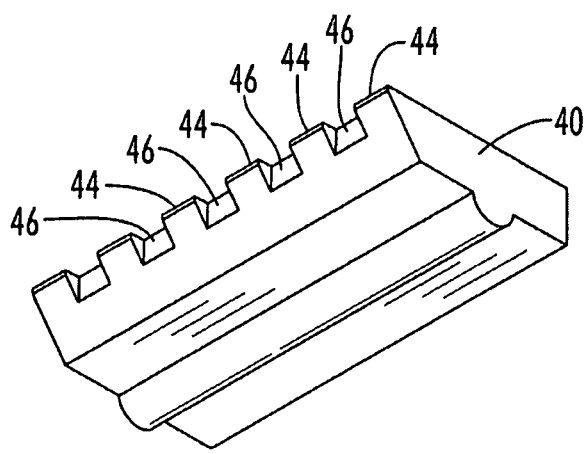
FIG. 9b is an illustration of a bottom view of a cutter insert of the present invention.

Referring now to FIGS. 9a and 9b, there is a first embodiment of cutter scrapper 40 for use in removing portions of bone stuck to cutter heads 30 of the present invention. Generally, cutter scrapper 40 includes teeth 44 alternated with recesses 46 which coincide with the rows of teeth and rows of smooth area on each cutter head for the removal of bone matter. Additionally, scrapper 40 may also include ridge 42 to assist in aligning the cutter scrapper 40 with the cutter heads of the present invention. In further embodiments, scrapper 40 may take on a variety of different embodiments including having a design on both ends so that both scrappers may engaged at once and furthermore may include a variety of teeth and recessed type designs to remove bone material that may be stuck or adhere to the cutter heads. In further embodiments, scrapper 40 assists in redistributing bone material so that the material may be ground again to produce the preferable size range bone particulate.

Figure 10:
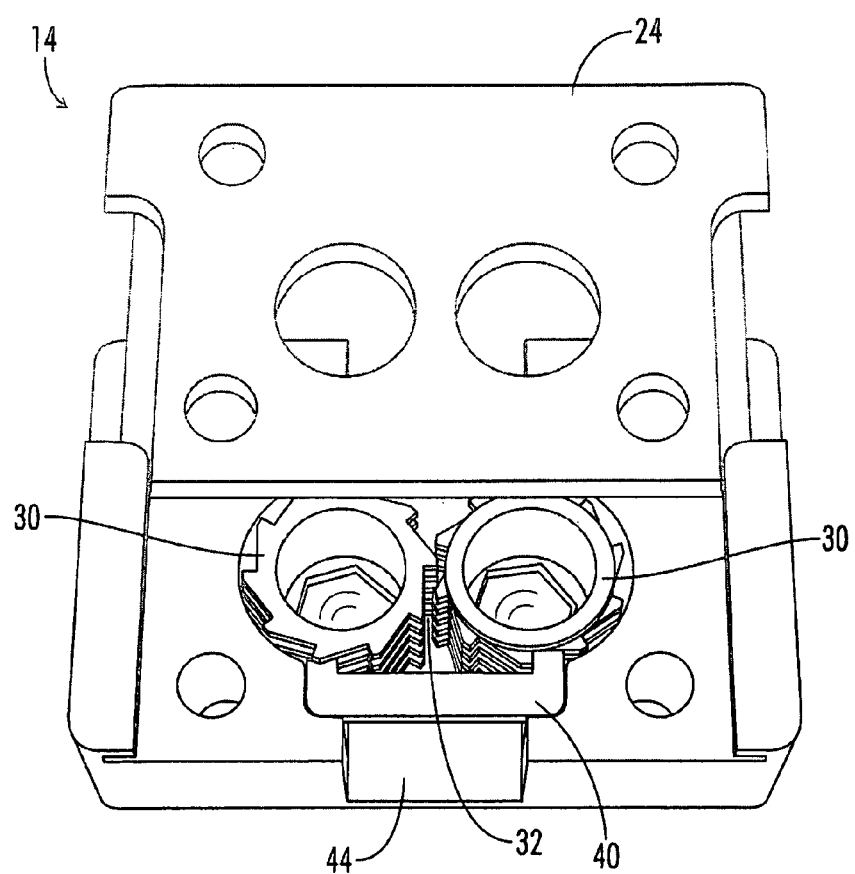
FIG. 10 is an illustration of the cutter unit with backing plate removed to show cutter heads with an embodiment of the cutter inserts of the present invention.

Referring now to FIG. 10 there is an illustration of cutter head unit 14 having backing plate 24 partially removed to display cutter unit 30, cutting zone 32, and scrapper 40. Generally, scrapper 40 is at the lower portion of cutter 30 and generally provides assistance for removing stuck bone material from the cutters during grinding. As is further illustrated, scraper 40 may be in the general area of bone output 44 where ground bone material exists from the cutter unit during the grinding process. In further embodiments, scrapper 40 may be located at the top area or side areas of the cutters to remove bone material though preferably is located near the lower portions of the cutters in scrapping the teeth areas.

Advantageously, the invention of the above-captioned application may be of a relatively small size so that the device may sit within an operating room where bone material may be ground prior to being used in a medical procedure. Generally the invention is less than about 8" in height, 6" in width and about 8" in length. More preferably, the invention is less than about 6" in height, 5" in length and about 3" in width. In preferable embodiments the cutter head unit is completely disposable so that the grinder may be used hospital surgical suite for specifically only one patient. Subsequent to using the bone grinder, the main body with mounting shafts can be draped or wiped clean and thus left in the operating room with the entire cutter assembly being disposed. The next patient would then require a new disposable cutter head assembly that would already be prepackaged and sterilized. Advantageously, a user would not have to clean and sterilize a cutter head through autoclave techniques which require extensive energy, time and labor. Yet furthermore, cutter heads designed for multiple uses would require significantly greater cost in designing the cutter head of higher grade steel and would have to be subsequently deconstructed for cleaning. In further embodiments, the cutter head unit as well as the collection receptacle would be both be disposable and be supplied the user in a pre-sterilized condition.

The use of the present invention provides the additionally less likelihood that contamination would occur to the ground bone sample as the ground bone sample could be processed within the surgical suite and immediately used in the specific medical procedure. Additionally, significantly less operating expenses and time would be required in cleaning and preparing the bone grinder for the next subsequent use as the entire cutter head unit could be disposable.

Preferably, a gap may purposefully be provided between the cutter head and the main body with seals about the various protrusions from the main body so that bone does not migrate within the main body housing. Furthermore, a gap between the cutter head unit of the main body additionally provides for sterile and clean procedure as there is less likelihood of bone particulate contaminating the main body of the bone grinder. As such, virtually all of the bone material is contained within the cutter head unit which may be considered to be disposable. Subsequently, a nurse or other user may drape or sterile wipe the main body of the cutter to insure sterile conditions exist for the next patient.

In yet further embodiments, the cutter heads may be of a significantly longer lasting design and may be considered non-disposable aspects of the bone grinder. In these further embodiments the bone grinder is of a generally small size and may be used in a tissue bank or other type location where large volumes of ground bone are required. Conversely, the bone grinder using the disposable cutter head unit generally are required to grind low volumes of bone for a patient and thus does not necessitate durable and long lasting cutter heads.

Generally, in a surgical suite the bone cutter of the present invention may be primarily used to grind cancellous bone. Cancellous bone is typically a lower density bone having a high surface area and houses the majority of arteries and veins within bones. The cutters as previously described function well in grinding cancellous bones, making the bone grinder of the present invention even more advantageous to use in a surgical environment. Generally, such bone is ground to chunks of from about 2 millimeters to about 16 millimeters. For instances where the grinder is utilized for grinding substantial amounts of cortical bone (such as in a tissue bank), the bone grinder of the present invention advantageously allows an individual to change the cutter head unit so that a unit having different style cutters may be used which may cut the specific type of bone more efficiently. Furthermore, a user has little to worry about cross-contaminating different bone grindings with one another as the ability to switch cutter head units maintains the bone particles within each individual cutter head unit.

Additionally, a variety of different bone composites may be created for use with the invention including bone composite material as described in U.S. Pat. No. 7,001,551 issued to the inventor of the present invention which is hereby incorporated by reference in its entirety. Furthermore, different bone composites may be utilized including composites including a growth accelerators so as to further promote localized bone growth about the implant upon implantation into a patient.

A final aspect of the present invention is that the one or both of the single use cutter heads utilized in grinding bone may also be utilized as an implanted surgical cage, meaning that the cutting tool of the novel bone grinder may be removed upon grinding bone and subsequently and directly implanted into a patient. As such, a variety of different materials may be utilized to comprise the cage including stainless steel, titanium, or PEEK, or a variety of other composites or metals useful for both a cutter and a cage material and the end of the cutter can be capped and screwed into place. One side of the cap may include a receptacle, socket, or fitting including an Allen head-type fitting so that a person may place the cutter between the vertebras. Generally, the cutting teeth of the cutting head may be closer in design to the cutter head of FIG.

8a where the teeth are positioned so that they are exposed to the open edges of the spine and do not primarily contact the vertebra. Once the cage is situated according to the surgeon's desires, the novel cutter cage may then be engaged with a tool such as an Allen wrench which fits in the receptacle or fitting on the cage so that the surgeon can then twist the cage preferably about 90 degrees so that the teeth on the cutter cage combination lock into each vertebral body. As such, the cage cutter tool combination is substantially fixed within the vertebra and thus functions as a typical cage although possesses the novel and unobvious qualities of being utilized as a cutter and subsequently as a cage. This provides a greater ease of operation and less potential for loss of ground bone as well as contamination of the cage as the cutter tool may be taken directly from the novel bone grinder and placed within the patient's body. Furthermore, as similar to the disposable nature of the previously described embodiments of the cutter head, the cutter head in this embodiment is also a single grinding cutter head.

Accordingly, by the practice of the present invention a bone grinder having heretofore unrecognized characteristics is described. The bone grinder exhibits exceptional utility as it may be placed within a surgical suite for operations. Furthermore, the bone grinder may use a disposable cutter head to significantly reduce the time and complications associated with cleaning bone grinders making the grinder of the present invention uniquely effective for medical procedures.

The disclosure of all cited patents and publications referred to in this application are incorporated herein by reference.

What is claimed is:

1. A bone grinder comprising:
    a main body with one or more mounting shafts and one or more drive shafts; and
    a removable cutter head unit attachable to the one or more mounting shafts with two or more cutting heads for engaging the drive shafts to grind bone within a cutting zone;
    a backing plate on the removable cutter head unit on the side of the removable cutter head unit adjacent to the main body of the bone grinder, the backing plate at least partially enclosing the two or more cutting heads within the removable cutter head unit; and
    the removable cutter head unit having a bone input and bone output separate from the main body of the bone grinder.

2. The bone grinder of claim 1 further comprising a ground bone receptacle located proximate to the bone output of the removable cutter head.

3. The bone grinder of claim 1 wherein the two or more cutting heads comprise a first cutting head and a second cutting head with each cutting head having teeth.

4. The bone grinder of claim 1 wherein the teeth of the first cutting head move in a first direction through the cutting zone and the teeth of the second cutting head move in a second direction through the cutting zone wherein the first direction and the second direction are similar.

5. The bone grinder of claim 1 wherein the teeth of the first cutting head move in a first direction through the cutting zone and the teeth of the second cutting head move in a second direction through the cutting zone wherein the first direction and the second direction are different.

6. The bone grinder of claim 1 wherein the removable cutter head unit further comprises one or more scrapers.

7. The bone grinder of claim 6 wherein the one or more scrapers are sized to fit closely to the cutter heads.

8. The bone grinder of claim 1 wherein the bone input is above the two or more cutting heads and the bone output is below the two or more cutting heads.

9. The bone grinder of claim 1 wherein the grinder is less than about 8 inches in height.

10. The bone grinder of claim 9 wherein the grinder is less than about 8 inches in height, less than about 8 inches in length and less then about 6 inches in width.

11. The bone grinder of claim 10 wherein the grinder is less than about 6 inches in height, less than about 5 inches in length and less than about 3 inches in width.

12. A bone grinder comprising:
    a main body with one or more mounting shafts and one or more drive shafts; and
    a removable cutter head unit attachable to the one or more mounting shafts comprising
    a bone input for inserting bone there into;
    two cutter heads below the bone input for grinding bone
    a bone output below the cutter heads for removing ground bone;
    a backing plate on the side of the removable cutter head unit adjacent to the main body of the bone grinder, the backing plate at least partially enclosing the two cutter heads within the removable cutter head unit and having aperatures for the one or more mounting shafts and the one or more drive shafts; and
    wherein the main body housing with one or more mounting shafts and one or more drive shafts remains substantially free of bone material.

13. The grinder of claim 12 further comprising a gap between the cutter head unit and the main body of the grinder.

14. A bone grinder comprising:
    a main body with one or more mounting shafts and one or more drive shafts; and
    a removable cutter head unit attachable to the one or more mounting shafts comprising
    a bone input for inserting bone there into;
    two cutter heads below the bone input for grinding bone
    a bone output below the cutter heads for removing ground bone;
    a backing plate on the side of the removable cutter head unit adjacent to the main body of the bone grinder, the backing plate at least partially enclosing the two cutter heads within the removable cutter head unit and having aperatures for the one or more mounting shafts and the one or more drive shafts;
    a ground bone receptacle located proximate to the bone output of the removable cutter head; and
    one or more scrapers sized to fit closely to the cutter heads;
    wherein the main body housing with one or more mounting shafts and one or more drive shafts remains substantially free of bone material.

* * * * *